United States Patent
Kawachi et al.

(10) Patent No.: US 6,496,723 B1
(45) Date of Patent: Dec. 17, 2002

(54) METHOD OF OBTAINING INFORMATION THAT CORRESPONDS TO ELECTROCARDIOGRAM OF HUMAN BODY FROM PULSE WAVE THEREOF

(75) Inventors: Taiji Kawachi, Kariya (JP); Tsuyoshi Nakagawa, Nagoya (JP); Teiyuu Kimura, Nagoya (JP); Rie Ohsaki, Anjo (JP)

(73) Assignee: Denso Corporation, Kariya (JP)

( * ) Notice: Subject to any disclaimer, the term of this patent is extended or adjusted under 35 U.S.C. 154(b) by 48 days.

(21) Appl. No.: 09/649,967

(22) Filed: Aug. 28, 2000

(30) Foreign Application Priority Data

Aug. 30, 1999 (JP) ............................. 11-242528
Sep. 1, 1999 (JP) ............................. 11-247264

(51) Int. Cl.⁷ ............................................. A61B 5/04
(52) U.S. Cl. .................................................. 600/517
(58) Field of Search ................. 600/509, 517, 600/519, 521, 514, 528; 607/4, 5, 9, 25

(56) References Cited

U.S. PATENT DOCUMENTS 4,263,919 A * 4/1981 Levin ..................... 128/708

FOREIGN PATENT DOCUMENTS

JP  5-288869   11/1993
JP  6-154177   6/1994
JP  7-299044   11/1995

* cited by examiner

Primary Examiner—Jeffrey R. Jastrzab
Assistant Examiner—Frances P. Oropeza
(74) Attorney, Agent, or Firm—Law Offices of David G. Posz (57) ABSTRACT

A method of obtaining information that corresponds to the R—R interval of electrocardiogram from the pulse-wave of a human body. The method is comprised of steps of detecting the pulse-wave of a human body in a predetermined period, differentiating the detected pulse-wave to provide a speed-pulse-wave, measuring intervals of peaks of the speed-pulse-wave, and substituting the intervals of peaks of the speed-pulse-wave for the R—R interval of the electrocardiogram.

17 Claims, 14 Drawing Sheets

NORMAL PULSE-WAVE

FIG. 3B

SPEED-PULSE-WAVE

| FIG. 5A |
|---------|
| FIG. 5B |

FIG. 5A (msec)

Data1-1

| Pt \ Ph | 0.35 | 0.30 | 0.25 | 0.20 | 0.15 | 0.10 | 0.05 |
|---------|------|------|------|------|------|------|------|
| 0.60 | 4.81 | 4.81 | 4.81 | 4.81 | 4.81 | 4.81 | 4.81 |
| 0.70 | 4.81 | 4.81 | 4.81 | 4.81 | 4.81 | 4.81 | 4.81 |
| 0.75 | 4.81 | 4.81 | 4.81 | 4.81 | 4.81 | 4.81 | 4.81 |
| 0.80 | 4.81 | 4.81 | 4.81 | 4.81 | 4.81 | 4.81 | 4.81 |
| 0.90 | 20.11 | 20.11 | 20.11 | 20.11 | 20.11 | 20.11 | 20.11 |

Data1-2

| Pt \ Ph | 0.35 | 0.30 | 0.25 | 0.20 | 0.15 | 0.10 | 0.05 |
|---------|------|------|------|------|------|------|------|
| 0.60 | 5.36 | 5.36 | 5.36 | 5.36 | 5.36 | 5.36 | 5.36 |
| 0.70 | 5.36 | 5.36 | 5.36 | 5.36 | 5.36 | 5.36 | 5.36 |
| 0.75 | 5.36 | 5.36 | 5.36 | 5.36 | 5.36 | 5.36 | 5.36 |
| 0.80 | 5.36 | 5.36 | 5.36 | 5.36 | 5.36 | 5.36 | 5.36 |
| 0.90 | 59.55 | 59.55 | 59.55 | 59.55 | 59.55 | 59.55 | 59.55 |

Data2-1

| Pt \ Ph | 0.35 | 0.30 | 0.25 | 0.20 | 0.15 | 0.10 | 0.05 |
|---------|------|------|------|------|------|------|------|
| 0.60 | 5.14 | 5.14 | 5.14 | 8.37 | 8.37 | 15.26 | 15.26 |
| 0.70 | 5.14 | 5.14 | 5.14 | 5.14 | 5.14 | 8.37 | 11.23 |
| 0.75 | 5.14 | 5.14 | 5.14 | 5.14 | 5.14 | 5.14 | 11.23 |
| 0.80 | 5.14 | 5.14 | 5.14 | 5.14 | 5.14 | 5.14 | 8.00 |
| 0.90 | 34.19 | 34.19 | 34.19 | 11.74 | 11.74 | 5.14 | 8.00 |

Data2-2

| Pt \ Ph | 0.35 | 0.30 | 0.25 | 0.20 | 0.15 | 0.10 | 0.05 |
|---------|------|------|------|------|------|------|------|
| 0.60 | 10.19 | 10.19 | 10.19 | 10.19 | 10.67 | 16.00 | 16.00 |
| 0.70 | 6.81 | 6.81 | 6.81 | 6.81 | 8.98 | 16.00 | 16.08 |
| 0.75 | 6.81 | 6.81 | 6.81 | 6.81 | 8.98 | 12.67 | 16.08 |
| 0.80 | 6.81 | 6.81 | 6.81 | 6.81 | 6.81 | 10.50 | 12.67 |
| 0.90 | 49.37 | 49.37 | 49.37 | 49.37 | 20.41 | 6.81 | 8.98 |

Data3-1

| Pt \ Ph | 0.35 | 0.30 | 0.25 | 0.20 | 0.15 | 0.10 | 0.05 |
|---------|------|------|------|------|------|------|------|
| 0.60 | 27.29 | 26.44 | 26.44 | 17.96 | 25.30 | 36.62 | 59.81 |
| 0.70 | 27.29 | 26.44 | 26.44 | 17.96 | 27.54 | 30.72 | 49.58 |
| 0.75 | 24.25 | 23.41 | 23.41 | 15.87 | 20.53 | 32.95 | 49.58 |
| 0.80 | 57.41 | 56.51 | 56.51 | 26.67 | 15.41 | 33.27 | 46.62 |
| 0.90 | 148.65 | 147.81 | 147.81 | 108.00 | 90.26 | 54.21 | 42.83 |

Data3-2

| Pt \ Ph | 0.35 | 0.30 | 0.25 | 0.20 | 0.15 | 0.10 | 0.05 |
|---------|------|------|------|------|------|------|------|
| 0.60 | 8.42 | 8.42 | 8.42 | 8.42 | 8.42 | 11.26 | 29.30 |
| 0.70 | 8.42 | 8.42 | 8.42 | 8.42 | 11.26 | 11.26 | 29.30 |
| 0.75 | 8.42 | 8.42 | 8.42 | 8.42 | 8.42 | 8.42 | 26.49 |
| 0.80 | 8.42 | 8.42 | 8.42 | 8.42 | 8.42 | 8.42 | 12.16 |
| 0.90 | 31.21 | 31.21 | 31.21 | 31.21 | 31.21 | 31.21 | 8.42 |

Data4-1

| Pt \ Ph | 0.35 | 0.30 | 0.25 | 0.20 | 0.15 | 0.10 | 0.05 |
|---------|------|------|------|------|------|------|------|
| 0.60 | 8.15 | 8.15 | 8.15 | 8.15 | 8.15 | 8.15 | 8.15 |
| 0.70 | 8.15 | 8.15 | 8.15 | 8.15 | 8.15 | 8.15 | 8.15 |
| 0.75 | 8.15 | 8.15 | 8.15 | 8.15 | 8.15 | 8.15 | 8.15 |
| 0.80 | 8.16 | 8.15 | 8.16 | 8.16 | 8.16 | 8.16 | 8.16 |
| 0.90 | 176.57 | 24.02 | 24.02 | 24.02 | 24.02 | 24.02 | 24.02 |

Data4-2

| Pt \ Ph | 0.35 | 0.30 | 0.25 | 0.20 | 0.15 | 0.10 | 0.05 |
|---------|------|------|------|------|------|------|------|
| 0.60 | 138.56 | 20.16 | 25.11 | 15.37 | 15.37 | 15.37 | 17.07 |
| 0.70 | 138.56 | 14.01 | 18.96 | 9.22 | 9.22 | 9.22 | 10.92 |
| 0.75 | 138.56 | 14.01 | 18.96 | 9.22 | 9.22 | 9.22 | 10.92 |
| 0.80 | 138.56 | 14.01 | 18.96 | 9.22 | 9.22 | 9.22 | 10.92 |
| 0.90 | 175.28 | 14.01 | 18.96 | 9.22 | 9.22 | 9.22 | 10.92 |

FIG. 5B (msec)

| Data1-3 | Ph | | | | | | |
|---|---|---|---|---|---|---|---|
| | | 0.35 | 0.30 | 0.25 | 0.20 | 0.15 | 0.10 | 0.05 |
| Pt | 0.60 | 125.42 | 65.80 | 65.33 | 24.18 | 8.32 | 8.32 | 9.12 |
| | 0.70 | 125.42 | 63.10 | 65.33 | 24.18 | 8.32 | 8.32 | 9.56 |
| | 0.75 | 125.42 | 63.10 | 65.33 | 24.18 | 8.32 | 8.32 | 9.56 |
| | 0.80 | 139.06 | 63.10 | 63.10 | 24.18 | 13.73 | 13.73 | 13.73 |
| | 0.90 | 316.87 | 197.94 | 145.68 | 105.02 | 76.35 | 76.35 | 60.70 |

| Data2-3 | Ph | | | | | | |
|---|---|---|---|---|---|---|---|
| | | 0.35 | 0.30 | 0.25 | 0.20 | 0.15 | 0.10 | 0.05 |
| Pt | 0.60 | 5.50 | 5.50 | 5.50 | 5.50 | 5.50 | 5.50 | 6.95 |
| | 0.70 | 5.50 | 5.50 | 5.50 | 5.50 | 5.50 | 5.50 | 6.95 |
| | 0.75 | 5.50 | 5.50 | 5.50 | 5.50 | 5.50 | 5.50 | 6.95 |
| | 0.80 | 5.50 | 5.50 | 5.50 | 5.50 | 5.50 | 5.50 | 6.95 |
| | 0.90 | 36.90 | 36.90 | 36.90 | 36.90 | 36.90 | 20.73 | 5.50 |

| Data3-3 | Ph | | | | | | |
|---|---|---|---|---|---|---|---|
| | | 0.35 | 0.30 | 0.25 | 0.20 | 0.15 | 0.10 | 0.05 |
| Pt | 0.60 | 7.86 | 7.86 | 7.86 | 7.86 | 7.86 | 12.94 | 22.05 |
| | 0.70 | 7.86 | 7.86 | 7.86 | 7.86 | 7.86 | 7.86 | 16.96 |
| | 0.75 | 7.86 | 7.86 | 7.86 | 7.86 | 7.86 | 7.86 | 12.44 |
| | 0.80 | 7.86 | 7.86 | 7.86 | 7.86 | 7.86 | 7.86 | 9.57 |
| | 0.90 | 19.06 | 19.06 | 19.06 | 19.06 | 19.06 | 19.06 | 7.86 |

| Data4-3 | Ph | | | | | | |
|---|---|---|---|---|---|---|---|
| | | 0.35 | 0.30 | 0.25 | 0.20 | 0.15 | 0.10 | 0.05 |
| Pt | 0.60 | 66.85 | 30.13 | 11.78 | 11.78 | 11.78 | 11.78 | 23.81 |
| | 0.70 | 66.85 | 30.13 | 11.78 | 11.78 | 11.78 | 11.78 | 15.85 |
| | 0.75 | 66.85 | 30.13 | 11.78 | 11.78 | 11.78 | 11.78 | 15.85 |
| | 0.80 | 91.02 | 57.69 | 39.35 | 39.35 | 39.35 | 39.35 | 15.85 |
| | 0.90 | 170.97 | 116.06 | 80.66 | 80.66 | 80.66 | 80.66 | 70.68 |

| M.V. | Ph | | | | | | |
|---|---|---|---|---|---|---|---|
| | | 0.35 | 0.30 | 0.25 | 0.20 | 0.15 | 0.10 | 0.05 |
| Pt | 0.60 | 45.75 | 16.50 | 15.34 | 10.90 | 10.23 | 12.04 | 18.14 |
| | 0.70 | 45.47 | 15.48 | 14.55 | 9.84 | 9.49 | 10.07 | 15.39 |
| | 0.75 | 45.21 | 15.23 | 14.29 | 9.43 | 8.67 | 10.02 | 14.79 |
| | 0.80 | 51.13 | 20.28 | 19.17 | 12.62 | 10.81 | 12.61 | 12.90 |
| | 0.90 | 103.23 | 62.52 | 55.63 | 46.24 | 39.96 | 33.92 | 25.96 |

FIG. 6

| FIG. 6A |
|---------|
| FIG. 6B |

FIG. 6A (msec)

Data1-1

| Pt \ Ph | 0.35 | 0.30 | 0.25 | 0.20 | 0.15 | 0.10 | 0.05 |
|---|---|---|---|---|---|---|---|
| 0.60 | 6.35 | 6.35 | 6.35 | 6.35 | 6.35 | 6.35 | 6.35 |
| 0.70 | 6.35 | 6.35 | 6.35 | 6.35 | 6.35 | 6.35 | 6.35 |
| 0.75 | 6.35 | 6.35 | 6.35 | 6.35 | 6.35 | 6.35 | 6.35 |
| 0.80 | 6.35 | 6.35 | 6.35 | 6.35 | 6.35 | 6.35 | 6.35 |
| 0.90 | 29.42 | 29.42 | 29.42 | 29.42 | 29.42 | 29.42 | 29.42 |

Data1-2

| Pt \ Ph | 0.35 | 0.30 | 0.25 | 0.20 | 0.15 | 0.10 | 0.05 |
|---|---|---|---|---|---|---|---|
| 0.60 | 7.98 | 7.98 | 7.98 | 7.98 | 7.98 | 7.98 | 7.98 |
| 0.70 | 7.98 | 7.98 | 7.98 | 7.98 | 7.98 | 7.98 | 7.98 |
| 0.75 | 7.98 | 7.98 | 7.98 | 7.98 | 7.98 | 7.98 | 7.98 |
| 0.80 | 7.98 | 7.98 | 7.98 | 7.98 | 7.98 | 7.98 | 7.98 |
| 0.90 | 68.70 | 68.70 | 68.70 | 68.70 | 68.70 | 68.70 | 68.70 |

Data2-1

| Pt \ Ph | 0.35 | 0.30 | 0.25 | 0.20 | 0.15 | 0.10 | 0.05 |
|---|---|---|---|---|---|---|---|
| 0.60 | 14.58 | 14.58 | 14.58 | 16.78 | 16.78 | 16.78 | 23.77 |
| 0.70 | 9.21 | 9.21 | 9.21 | 11.38 | 11.38 | 11.38 | 18.77 |
| 0.75 | 9.21 | 9.21 | 9.21 | 9.21 | 9.21 | 9.21 | 18.77 |
| 0.80 | 9.21 | 9.21 | 9.21 | 9.21 | 9.21 | 9.21 | 13.38 |
| 0.90 | 23.11 | 23.11 | 23.11 | 22.85 | 9.33 | 9.33 | 11.20 |

Data2-2

| Pt \ Ph | 0.35 | 0.30 | 0.25 | 0.20 | 0.15 | 0.10 | 0.05 |
|---|---|---|---|---|---|---|---|
| 0.60 | 11.88 | 11.88 | 11.88 | 11.88 | 14.97 | 16.51 | 25.58 |
| 0.70 | 9.16 | 9.16 | 9.16 | 9.16 | 10.64 | 18.71 | 18.71 |
| 0.75 | 9.16 | 9.16 | 9.16 | 9.16 | 10.64 | 14.39 | 18.71 |
| 0.80 | 9.16 | 9.16 | 9.16 | 9.16 | 10.64 | 13.25 | 14.39 |
| 0.90 | 67.99 | 67.99 | 67.99 | 67.99 | 16.40 | 9.16 | 13.25 |

Data3-1

| Pt \ Ph | 0.35 | 0.30 | 0.25 | 0.20 | 0.15 | 0.10 | 0.05 |
|---|---|---|---|---|---|---|---|
| 0.60 | 41.60 | 41.60 | 41.60 | 32.82 | 29.94 | 37.88 | 65.90 |
| 0.70 | 41.60 | 41.60 | 41.60 | 32.82 | 32.02 | 39.96 | 46.62 |
| 0.75 | 41.60 | 41.60 | 41.60 | 32.93 | 23.28 | 33.06 | 44.00 |
| 0.80 | 62.05 | 62.05 | 62.05 | 45.98 | 23.28 | 26.12 | 46.20 |
| 0.90 | 150.52 | 150.52 | 150.52 | 114.53 | 86.14 | 43.85 | 40.30 |

Data3-2

| Pt \ Ph | 0.35 | 0.30 | 0.25 | 0.20 | 0.15 | 0.10 | 0.05 |
|---|---|---|---|---|---|---|---|
| 0.60 | 12.28 | 12.28 | 12.28 | 14.49 | 14.49 | 14.49 | 24.70 |
| 0.70 | 12.28 | 12.28 | 12.28 | 14.49 | 14.49 | 14.49 | 24.70 |
| 0.75 | 12.28 | 12.28 | 12.28 | 14.49 | 14.49 | 14.49 | 24.70 |
| 0.80 | 12.28 | 12.28 | 12.28 | 12.28 | 12.28 | 12.28 | 24.70 |
| 0.90 | 45.97 | 45.97 | 45.97 | 43.86 | 43.86 | 43.86 | 13.96 |

Data4-1

| Pt \ Ph | 0.35 | 0.30 | 0.25 | 0.20 | 0.15 | 0.10 | 0.05 |
|---|---|---|---|---|---|---|---|
| 0.60 | 8.83 | 8.83 | 8.83 | 8.83 | 8.83 | 8.83 | 8.83 |
| 0.70 | 8.83 | 8.83 | 8.83 | 8.83 | 8.83 | 8.83 | 8.83 |
| 0.75 | 144.88 | 8.83 | 8.83 | 8.85 | 8.85 | 8.85 | 8.85 |
| 0.80 | 144.88 | 8.85 | 8.85 | 8.85 | 8.85 | 8.85 | 8.85 |
| 0.90 | 178.31 | 24.90 | 24.90 | 24.90 | 24.90 | 24.90 | 29.42 |

Data4-2

| Pt \ Ph | 0.35 | 0.30 | 0.25 | 0.20 | 0.15 | 0.10 | 0.05 |
|---|---|---|---|---|---|---|---|
| 0.60 | 151.93 | 19.43 | 23.82 | 14.17 | 14.17 | 14.17 | 15.06 |
| 0.70 | 151.93 | 19.43 | 23.82 | 14.17 | 14.17 | 14.17 | 15.06 |
| 0.75 | 151.93 | 19.43 | 23.82 | 14.17 | 14.17 | 14.17 | 15.06 |
| 0.80 | 151.93 | 19.43 | 23.82 | 14.17 | 14.17 | 14.17 | 15.06 |
| 0.90 | 169.39 | 19.43 | 23.82 | 14.17 | 14.17 | 14.17 | 15.06 |

FIG. 6B (msec)

| Data1-3 | Ph | | | | | | |
|---|---|---|---|---|---|---|---|
| | 0.35 | 0.30 | 0.25 | 0.20 | 0.15 | 0.10 | 0.05 |
| Pt 0.60 | 123.86 | 64.30 | 65.89 | 25.67 | 9.10 | 9.10 | 14.64 |
| 0.70 | 123.86 | 64.30 | 65.89 | 25.67 | 9.10 | 9.10 | 9.89 |
| 0.75 | 123.86 | 64.30 | 65.89 | 25.67 | 9.10 | 9.10 | 9.89 |
| 0.80 | 123.86 | 64.30 | 65.28 | 25.06 | 8.49 | 8.49 | 9.89 |
| 0.90 | 276.94 | 168.63 | 144.16 | 90.52 | 61.58 | 61.58 | 48.26 |

| Data2-3 | Ph | | | | | | |
|---|---|---|---|---|---|---|---|
| | 0.35 | 0.30 | 0.25 | 0.20 | 0.15 | 0.10 | 0.05 |
| Pt 0.60 | 8.60 | 8.60 | 8.60 | 8.60 | 8.60 | 8.60 | 9.35 |
| 0.70 | 8.60 | 8.60 | 8.60 | 8.60 | 8.60 | 8.60 | 9.35 |
| 0.75 | 8.60 | 8.60 | 8.60 | 8.60 | 8.60 | 8.60 | 9.35 |
| 0.80 | 8.60 | 8.60 | 8.60 | 8.60 | 8.60 | 8.60 | 9.35 |
| 0.90 | 39.56 | 39.56 | 39.56 | 39.56 | 39.56 | 39.56 | 9.35 |

| Data3-3 | Ph | | | | | | |
|---|---|---|---|---|---|---|---|
| | 0.35 | 0.30 | 0.25 | 0.20 | 0.15 | 0.10 | 0.05 |
| Pt 0.60 | 13.01 | 13.01 | 13.01 | 13.01 | 13.01 | 16.47 | 21.65 |
| 0.70 | 13.01 | 13.01 | 13.01 | 13.01 | 13.01 | 13.01 | 18.19 |
| 0.75 | 13.01 | 13.01 | 13.01 | 13.01 | 13.01 | 13.01 | 18.19 |
| 0.80 | 13.01 | 13.01 | 13.01 | 13.01 | 13.01 | 13.01 | 18.19 |
| 0.90 | 13.01 | 13.01 | 13.01 | 13.01 | 13.01 | 13.01 | 14.70 |

| Data4-3 | Ph | | | | | | |
|---|---|---|---|---|---|---|---|
| | 0.35 | 0.30 | 0.25 | 0.20 | 0.15 | 0.10 | 0.05 |
| Pt 0.60 | 109.68 | 72.64 | 53.51 | 36.71 | 36.71 | 17.27 | 23.98 |
| 0.70 | 109.68 | 72.64 | 53.51 | 36.71 | 36.71 | 17.27 | 17.27 |
| 0.75 | 109.68 | 72.64 | 53.51 | 36.71 | 36.71 | 17.27 | 17.27 |
| 0.80 | 137.70 | 85.47 | 66.33 | 49.54 | 49.54 | 30.09 | 17.27 |
| 0.90 | 265.61 | 211.03 | 140.25 | 121.14 | 121.14 | 101.69 | 45.28 |

| M.V. | Ph | | | | | | |
|---|---|---|---|---|---|---|---|
| | 0.35 | 0.30 | 0.25 | 0.20 | 0.15 | 0.10 | 0.05 |
| Pt 0.60 | 53.89 | 23.46 | 22.36 | 16.44 | 15.08 | 14.54 | 20.65 |
| 0.70 | 53.21 | 22.78 | 21.69 | 15.76 | 14.44 | 14.15 | 16.81 |
| 0.75 | 53.21 | 22.78 | 21.69 | 15.59 | 13.53 | 13.04 | 16.59 |
| 0.80 | 57.25 | 25.56 | 24.41 | 17.52 | 14.37 | 13.20 | 15.97 |
| 0.90 | 110.71 | 71.86 | 64.28 | 54.22 | 45.14 | 38.27 | 26.53 |

FIG. 7

| FIG. 7A |
|---|
| FIG. 7B |

FIG. 7A

Data1-1 Ph (msec)

| Pt \ Ph | 0.35 | 0.30 | 0.25 | 0.20 | 0.15 | 0.10 | 0.05 |
|---|---|---|---|---|---|---|---|
| 0.60 | 5.64 | 5.64 | 5.64 | 5.64 | 5.64 | 5.64 | 5.64 |
| 0.70 | 5.64 | 5.64 | 5.64 | 5.64 | 5.64 | 5.64 | 5.64 |
| 0.75 | 5.64 | 5.64 | 5.64 | 5.64 | 5.64 | 5.64 | 5.64 |
| 0.80 | 5.64 | 5.64 | 5.64 | 5.64 | 5.64 | 5.64 | 5.64 |
| 0.90 | 20.56 | 20.56 | 20.56 | 20.56 | 20.56 | 20.56 | 20.56 |

Data2-1 Ph

| Pt \ Ph | 0.35 | 0.30 | 0.25 | 0.20 | 0.15 | 0.10 | 0.05 |
|---|---|---|---|---|---|---|---|
| 0.60 | 4.98 | 4.98 | 4.98 | 4.98 | 4.98 | 8.94 | 12.60 |
| 0.70 | 4.98 | 4.98 | 4.98 | 4.98 | 4.98 | 4.98 | 12.60 |
| 0.75 | 4.98 | 4.98 | 4.98 | 4.98 | 4.98 | 4.98 | 8.64 |
| 0.80 | 4.98 | 4.98 | 4.98 | 4.98 | 4.98 | 4.98 | 8.64 |
| 0.90 | 140.11 | 26.70 | 11.79 | 11.79 | 11.79 | 4.98 | 4.98 |

Data3-1 Ph

| Pt \ Ph | 0.35 | 0.30 | 0.25 | 0.20 | 0.15 | 0.10 | 0.05 |
|---|---|---|---|---|---|---|---|
| 0.60 | 33.63 | 33.63 | 33.63 | 26.73 | 31.69 | 42.23 | 64.53 |
| 0.70 | 33.63 | 33.63 | 33.63 | 23.14 | 28.11 | 38.60 | 62.45 |
| 0.75 | 33.63 | 33.63 | 33.63 | 23.14 | 23.14 | 33.30 | 62.45 |
| 0.80 | 58.51 | 58.51 | 58.51 | 41.02 | 23.14 | 26.34 | 56.18 |
| 0.90 | 140.11 | 140.11 | 140.11 | 117.82 | 82.21 | 47.21 | 40.60 |

Data4-1 Ph

| Pt \ Ph | 0.35 | 0.30 | 0.25 | 0.20 | 0.15 | 0.10 | 0.05 |
|---|---|---|---|---|---|---|---|
| 0.60 | 157.08 | 17.65 | 17.65 | 17.65 | 17.65 | 17.65 | 17.65 |
| 0.70 | 157.08 | 17.65 | 17.65 | 17.65 | 17.65 | 17.65 | 17.65 |
| 0.75 | 157.08 | 17.65 | 17.65 | 17.65 | 17.65 | 17.65 | 17.65 |
| 0.80 | 157.08 | 17.65 | 17.65 | 17.65 | 17.65 | 17.65 | 17.65 |
| 0.90 | 225.65 | 53.61 | 53.61 | 53.61 | 53.61 | 53.61 | 17.65 |

Data1-2 Ph (msec)

| Pt \ Ph | 0.35 | 0.30 | 0.25 | 0.20 | 0.15 | 0.10 | 0.05 |
|---|---|---|---|---|---|---|---|
| 0.60 | 5.81 | 5.81 | 5.81 | 5.81 | 5.81 | 5.81 | 5.81 |
| 0.70 | 5.81 | 5.81 | 5.81 | 5.81 | 5.81 | 5.81 | 5.81 |
| 0.75 | 5.81 | 5.81 | 5.81 | 5.81 | 5.81 | 5.81 | 5.81 |
| 0.80 | 5.81 | 5.81 | 5.81 | 5.81 | 5.81 | 5.81 | 5.81 |
| 0.90 | 51.52 | 51.52 | 51.52 | 51.52 | 51.52 | 51.52 | 51.52 |

Data2-2 Ph

| Pt \ Ph | 0.35 | 0.30 | 0.25 | 0.20 | 0.15 | 0.10 | 0.05 |
|---|---|---|---|---|---|---|---|
| 0.60 | 4.74 | 4.74 | 4.74 | 4.74 | 8.38 | 15.10 | 15.10 |
| 0.70 | 4.74 | 4.74 | 4.74 | 4.74 | 4.74 | 15.37 | 12.76 |
| 0.75 | 4.74 | 4.74 | 4.74 | 4.74 | 4.74 | 9.12 | 15.37 |
| 0.80 | 4.74 | 4.74 | 4.74 | 4.74 | 4.74 | 4.74 | 9.12 |
| 0.90 | 79.67 | 79.67 | 79.67 | 48.30 | 18.85 | 4.74 | 4.74 |

Data3-2 Ph

| Pt \ Ph | 0.35 | 0.30 | 0.25 | 0.20 | 0.15 | 0.10 | 0.05 |
|---|---|---|---|---|---|---|---|
| 0.60 | 15.39 | 15.39 | 15.39 | 18.59 | 18.59 | 47.16 | 15.39 |
| 0.70 | 15.39 | 15.39 | 15.39 | 15.39 | 15.39 | 24.77 | 15.39 |
| 0.75 | 15.39 | 15.39 | 15.39 | 15.39 | 15.39 | 15.39 | 15.39 |
| 0.80 | 15.39 | 15.39 | 15.39 | 15.39 | 15.39 | 15.39 | 15.39 |
| 0.90 | 27.18 | 27.18 | 27.18 | 24.21 | 24.21 | 15.39 | 15.39 |

Data4-2 Ph

| Pt \ Ph | 0.35 | 0.30 | 0.25 | 0.20 | 0.15 | 0.10 | 0.05 |
|---|---|---|---|---|---|---|---|
| 0.60 | 180.85 | 32.25 | 37.01 | 28.16 | 28.16 | 31.63 | 31.63 |
| 0.70 | 194.93 | 32.25 | 37.01 | 28.16 | 28.16 | 31.63 | 31.63 |
| 0.75 | 194.93 | 43.92 | 48.68 | 39.84 | 39.84 | 28.16 | 28.16 |
| 0.80 | 194.93 | 43.92 | 48.68 | 39.84 | 39.84 | 39.84 | 39.84 |
| 0.90 | 221.07 | 90.75 | 95.51 | 86.67 | 86.67 | 52.29 | 52.29 |

FIG. 7B (msec)

| Data1-3 | Ph | | | | | | |
|---|---|---|---|---|---|---|---|
| | | 0.35 | 0.30 | 0.25 | 0.20 | 0.15 | 0.10 | 0.05 |
| Pt | 0.60 | 132.18 | 68.36 | 69.00 | 27.37 | 9.59 | 9.59 | 10.32 |
| | 0.70 | 132.18 | 68.36 | 69.00 | 27.37 | 9.59 | 9.59 | 9.59 |
| | 0.75 | 132.18 | 68.36 | 69.00 | 27.37 | 9.59 | 9.59 | 9.59 |
| | 0.80 | 144.96 | 78.33 | 78.33 | 29.58 | 20.06 | 20.06 | 15.07 |
| | 0.90 | 286.48 | 194.59 | 187.42 | 115.89 | 93.49 | 93.49 | 63.40 |

| Data2-3 | Ph | | | | | | |
|---|---|---|---|---|---|---|---|
| | | 0.35 | 0.30 | 0.25 | 0.20 | 0.15 | 0.10 | 0.05 |
| Pt | 0.60 | 4.66 | 4.66 | 4.66 | 4.66 | 4.66 | 4.66 | 6.53 |
| | 0.70 | 4.66 | 4.66 | 4.66 | 4.66 | 4.66 | 4.66 | 6.53 |
| | 0.75 | 4.66 | 4.66 | 4.66 | 4.66 | 4.66 | 4.66 | 6.53 |
| | 0.80 | 4.66 | 4.66 | 4.66 | 4.66 | 4.66 | 4.66 | 6.53 |
| | 0.90 | 4.66 | 4.66 | 4.66 | 4.66 | 4.66 | 4.66 | 4.66 |

| Data3-3 | Ph | | | | | | |
|---|---|---|---|---|---|---|---|
| | | 0.35 | 0.30 | 0.25 | 0.20 | 0.15 | 0.10 | 0.05 |
| Pt | 0.60 | 12.84 | 12.84 | 12.84 | 12.84 | 12.84 | 12.84 | 26.56 |
| | 0.70 | 12.84 | 12.84 | 12.84 | 12.84 | 12.84 | 12.84 | 16.14 |
| | 0.75 | 12.84 | 12.84 | 12.84 | 12.84 | 12.84 | 12.84 | 16.14 |
| | 0.80 | 12.84 | 12.84 | 12.84 | 12.84 | 12.84 | 12.84 | 12.84 |
| | 0.90 | 12.84 | 12.84 | 12.84 | 12.84 | 12.84 | 12.84 | 12.84 |

| Data4-3 | Ph | | | | | | |
|---|---|---|---|---|---|---|---|
| | | 0.35 | 0.30 | 0.25 | 0.20 | 0.15 | 0.10 | 0.05 |
| Pt | 0.60 | 92.06 | 56.40 | 39.81 | 39.81 | 39.81 | 39.81 | 39.81 |
| | 0.70 | 102.66 | 67.01 | 50.41 | 50.41 | 50.41 | 50.41 | 39.81 |
| | 0.75 | 102.66 | 67.01 | 50.41 | 50.41 | 50.41 | 50.41 | 50.41 |
| | 0.80 | 127.16 | 91.50 | 50.41 | 50.41 | 50.41 | 50.41 | 50.41 |
| | 0.90 | 231.31 | 164.75 | 148.16 | 148.16 | 148.16 | 148.16 | 74.91 |

| M.V. | Ph | | | | | | |
|---|---|---|---|---|---|---|---|
| | | 0.35 | 0.30 | 0.25 | 0.20 | 0.15 | 0.10 | 0.05 |
| Pt | 0.60 | 54.16 | 21.86 | 20.93 | 16.42 | 15.65 | 17.42 | 23.61 |
| | 0.70 | 56.21 | 22.75 | 21.81 | 16.73 | 15.67 | 17.43 | 20.45 |
| | 0.75 | 56.21 | 23.72 | 22.79 | 17.71 | 16.22 | 17.44 | 20.15 |
| | 0.80 | 61.39 | 28.66 | 25.64 | 19.38 | 17.10 | 17.36 | 20.26 |
| | 0.90 | 110.65 | 72.25 | 69.42 | 58.00 | 50.71 | 46.05 | 30.30 |

FIG. 8

| Data1-1 | Ph | | | | | (msec) |
|---|---|---|---|---|---|---|
| Pt | 0.20 | 0.19 | 0.18 | 0.17 | 0.16 | 0.15 |
| 0.70 | 4.81 | 4.81 | 4.81 | 4.81 | 4.81 | 4.81 |
| 0.75 | 4.81 | 4.81 | 4.81 | 4.81 | 4.81 | 4.81 |
| 0.80 | 4.81 | 4.81 | 4.81 | 4.81 | 4.81 | 4.81 |

| Data1-2 | Ph | | | | | |
|---|---|---|---|---|---|---|
| Pt | 0.20 | 0.19 | 0.18 | 0.17 | 0.16 | 0.15 |
| 0.70 | 5.36 | 5.36 | 5.36 | 5.36 | 5.36 | 5.36 |
| 0.75 | 5.36 | 5.36 | 5.36 | 5.36 | 5.36 | 5.36 |
| 0.80 | 5.36 | 5.36 | 5.36 | 5.36 | 5.36 | 5.36 |

| Data1-3 | Ph | | | | | |
|---|---|---|---|---|---|---|
| Pt | 0.20 | 0.19 | 0.18 | 0.17 | 0.16 | 0.15 |
| 0.70 | 24.18 | 13.48 | 13.48 | 8.32 | 8.32 | 8.32 |
| 0.75 | 24.18 | 13.48 | 13.48 | 8.32 | 8.32 | 8.32 |
| 0.80 | 13.73 | 13.73 | 13.48 | 8.32 | 8.32 | 8.32 |

| Data2-1 | Ph | | | | | |
|---|---|---|---|---|---|---|
| Pt | 0.20 | 0.19 | 0.18 | 0.17 | 0.16 | 0.15 |
| 0.70 | 5.14 | 5.14 | 5.14 | 5.14 | 5.14 | 5.14 |
| 0.75 | 5.14 | 5.14 | 5.14 | 5.14 | 5.14 | 5.14 |
| 0.80 | 5.14 | 5.14 | 5.14 | 5.14 | 5.14 | 5.14 |

| Data2-2 | Ph | | | | | |
|---|---|---|---|---|---|---|
| Pt | 0.20 | 0.19 | 0.18 | 0.17 | 0.16 | 0.15 |
| 0.70 | 6.81 | 6.81 | 6.81 | 6.81 | 6.81 | 6.81 |
| 0.75 | 8.98 | 8.98 | 8.98 | 8.98 | 8.98 | 8.98 |
| 0.80 | 6.81 | 6.81 | 6.81 | 6.81 | 6.81 | 6.81 |

| Data2-3 | Ph | | | | | |
|---|---|---|---|---|---|---|
| Pt | 0.20 | 0.19 | 0.18 | 0.17 | 0.16 | 0.15 |
| 0.70 | 5.50 | 5.50 | 5.50 | 5.50 | 5.50 | 5.50 |
| 0.75 | 5.50 | 5.50 | 5.50 | 5.50 | 5.50 | 5.50 |
| 0.80 | 5.50 | 5.50 | 5.50 | 5.50 | 5.50 | 5.50 |

| Data3-1 | Ph | | | | | |
|---|---|---|---|---|---|---|
| Pt | 0.20 | 0.19 | 0.18 | 0.17 | 0.16 | 0.15 |
| 0.70 | 17.96 | 17.96 | 17.96 | 15.87 | 15.87 | 15.87 |
| 0.75 | 15.87 | 15.87 | 20.48 | 20.48 | 20.53 | 20.53 |
| 0.80 | 26.67 | 26.67 | 38.22 | 27.54 | 20.53 | 15.41 |

| Data3-2 | Ph | | | | | |
|---|---|---|---|---|---|---|
| Pt | 0.20 | 0.19 | 0.18 | 0.17 | 0.16 | 0.15 |
| 0.70 | 11.26 | 11.26 | 11.26 | 11.26 | 11.26 | 11.26 |
| 0.75 | 8.42 | 8.42 | 8.42 | 8.42 | 8.42 | 8.42 |
| 0.80 | 8.42 | 8.42 | 8.42 | 8.42 | 8.42 | 8.42 |

| Data3-3 | Ph | | | | | |
|---|---|---|---|---|---|---|
| Pt | 0.20 | 0.19 | 0.18 | 0.17 | 0.16 | 0.15 |
| 0.70 | 7.86 | 7.86 | 7.86 | 7.86 | 7.86 | 7.86 |
| 0.75 | 7.86 | 7.86 | 7.86 | 7.86 | 7.86 | 7.86 |
| 0.80 | 7.86 | 7.86 | 7.86 | 7.86 | 7.86 | 7.86 |

| Data4-1 | Ph | | | | | |
|---|---|---|---|---|---|---|
| Pt | 0.20 | 0.19 | 0.18 | 0.17 | 0.16 | 0.15 |
| 0.70 | 8.15 | 8.15 | 8.15 | 8.15 | 8.15 | 8.15 |
| 0.75 | 8.15 | 8.15 | 8.15 | 8.15 | 8.15 | 8.15 |
| 0.80 | 8.16 | 8.16 | 8.16 | 8.16 | 8.16 | 8.16 |

| Data4-2 | Ph | | | | | |
|---|---|---|---|---|---|---|
| Pt | 0.20 | 0.19 | 0.18 | 0.17 | 0.16 | 0.15 |
| 0.70 | 9.22 | 9.22 | 9.22 | 9.22 | 9.22 | 9.22 |
| 0.75 | 9.22 | 9.22 | 9.22 | 9.22 | 9.22 | 9.22 |
| 0.80 | 9.22 | 9.22 | 9.22 | 9.22 | 9.22 | 9.22 |

| Data4-3 | Ph | | | | | |
|---|---|---|---|---|---|---|
| Pt | 0.20 | 0.19 | 0.18 | 0.17 | 0.16 | 0.15 |
| 0.70 | 11.78 | 11.78 | 11.78 | 11.78 | 11.78 | 11.78 |
| 0.75 | 11.78 | 11.78 | 11.78 | 11.78 | 11.78 | 11.78 |
| 0.80 | 39.35 | 39.35 | 39.35 | 39.35 | 39.35 | 39.35 |

| M.V. | Ph | | | | | |
|---|---|---|---|---|---|---|
| Pt | 0.20 | 0.19 | 0.18 | 0.17 | 0.16 | 0.15 |
| 0.70 | 9.84 | 8.94 | 8.94 | 8.91 | 8.91 | 9.49 |
| 0.75 | 9.43 | 8.53 | 8.71 | 8.49 | 8.49 | 8.67 |
| 0.80 | 12.62 | 11.73 | 12.73 | 12.72 | 10.81 | 10.81 |

METHOD OF OBTAINING INFORMATION THAT CORRESPONDS TO ELECTROCARDIOGRAM OF HUMAN BODY FROM PULSE WAVE THEREOF

CROSS REFERENCE TO RELATED APPLICATION

The present application is based on and claims priority from Japanese Patent Applications: Hei 11-242528, filed Aug. 30, 1999 and Hei 11-247264, filed Sep. 1, 1999, the contents of which are incorporated herein by reference.

BACKGROUND OF THE INVENTION

1. Field of the Invention

The present invention relates to a method of obtaining information that corresponds to the R—R interval of the electrocardiogram of a human body for medical and health examinations.

2. Description of the Related Art

The electrocardiogram has been used for medical and health examinations. Particularly, the R—R intervals of the electrocardiogram have been frequently used to examine the heart beat rhythm and the automatic nervous system. The R-R intervals of the electrocardiogram are obtained from intervals of peak values of the R-wave that are most significantly observed in the QRS group, which is caused by depolarization of the ventricle.

On the other hand, it is considered to utilize the peak intervals between the pulse wavers peak values of the human-body as the information that corresponds to the R—R intervals of the electrocardiogram.

Because the peak values of the pulse-waves are not so clear as the peak values of the R-wave, it has been difficult to accurately determine the peak intervals of the pulse-wave.

A commonly used pulse-wave sensor measures a pulse-wave of a human body by means of light absorbing characteristics of hemoglobin of the blood. Such a pulse-wave sensor includes a light-emitting element for emitting light to a finger and light sensing element for sensing the light reflected from the finger.

While such a pulse-wave sensor is attached to a human finger, the sensor always moves as the human body moves. This motion causes noises, which are included in the pulse-wave data. In particular, when a shoulder or an elbow moves, the quantity of the blood changes, thereby causing noises. It has been also difficult to eliminate, from such a pulse-wave sensor, noises caused by outside light such as sunshine or light of lamps.

SUMMARY OF THE INVENTION

Therefore, a main object of the invention is to provide an improved method of measuring pulse-waves that is effective to provide practically accurate information that can be substituted for the R—R intervals of the electrocardiogram.

According to a main feature of the invention, a method of obtaining information that corresponds to the R—R interval of electrocardiogram from the pulse-wave of a human body is comprised of differentiating the pulse-wave to provide a speed-pulse-wave (differentiated pulse-wave), and measuring the intervals of peaks of the speed-pulse-wave. The intervals of peaks of the speed-pulse-wave practically approximate the R—R interval of the cardiogram.

In the meantime, the bottom interval of the pulse waves corresponds to the interval between consecutive times when the speed-pulse-wave changes from a negative to a positive. While, the peak interval of the pulse-waves corresponds to the interval between consecutive times when the speed-pulse-wave changes from a positive to a negative.

Another object of the invention is to provide a method of measuring a pulse-wave that can detect noises included in the pulse-wave data.

According to another feature of the invention, a method of measuring a pulse-wave is comprised of differentiating the pulse-wave to provide a speed-pulse-wave, detecting peak values of the speed-pulse-wave, calculating the dispersion of said peak values and comparing the dispersion with a predetermined value to determine whether a noise is included in the pulse-wave or not.

BRIEF DESCRIPTION OF THE DRAWINGS

Other objects, features and characteristics of the present invention as well as the functions of related parts of the present invention will become clear from a study of the following detailed description, the appended claims and the drawings. In the drawings:

FIGS. 5A and 5B are a table showing test results;

FIGS. 7A and 7B are a table showing test results;

DETAILED DESCRIPTION OF THE PREFERRED EMBODIMENTS

A method of obtaining information according to a first embodiment of the invention is described with reference to FIGS. 1–8. The information corresponds to the R-R interval of the electrocardiogram applied to a diagnosis system for a medical or health examination that is conducted to find out an arrhythmia or a disorder of the autonomic nerve system.

Figure 2A:
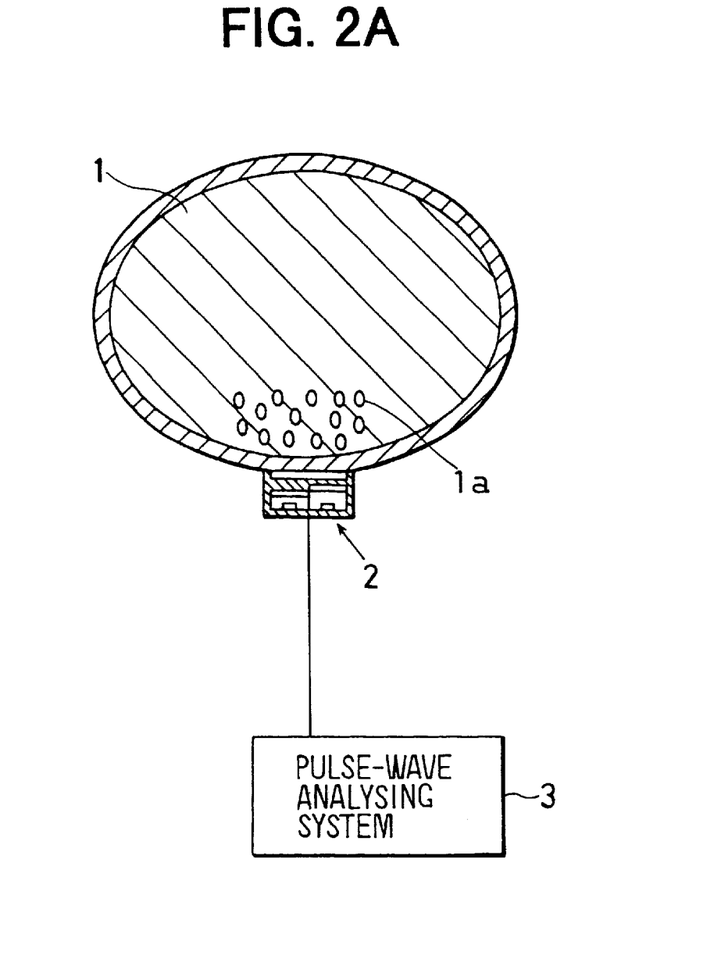
FIGS. 2A and 2B are cross-sectional schematic diagrams illustrating a finger and a pulse-wave sensor.
Figure 2B:
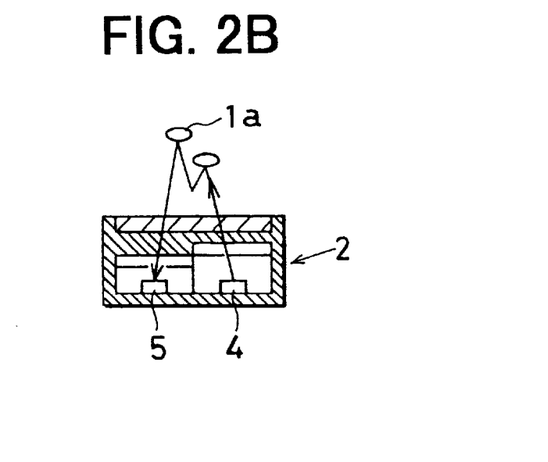

As shown in FIGS. 2A and 2B, the diagnosis system includes pulse-wave sensor 2 that is to be put on a finger 1 of a person and a pulse-wave-analyzing device 3. Pulse-wave sensor 2 is a light reflecting type sensor that is comprised of light emitting element 3 and light sensing element 4. If light is emitted from light emitting element 3 toward the finger 1, a portion of the light hit capillary 1a in the finger 1. A portion of the light is absorbed into hemoglobin of the blood passing the capillary 1a. The remainder of the light is scattered at the capillary 1a, a portion of which goes to light sensing element 4. Because the quantity of the hemoglobin in the capillary 1a changes due to pulsation of the blood, the amount of light absorbed in the blood changes in response to the pulsation so that the output voltage of the light sensing element 4 changes. This output voltage is sent to pulse-wave-analyzing device 3 as pulse-wave information shown in FIG. 3A.

Pulse-wave-analyzing device 3 includes a microcomputer with a pulse-wave-analyzing program for obtaining the pulse-wave R—R interval from the output voltage of pulse-wave sensor 2.

Figure 1:
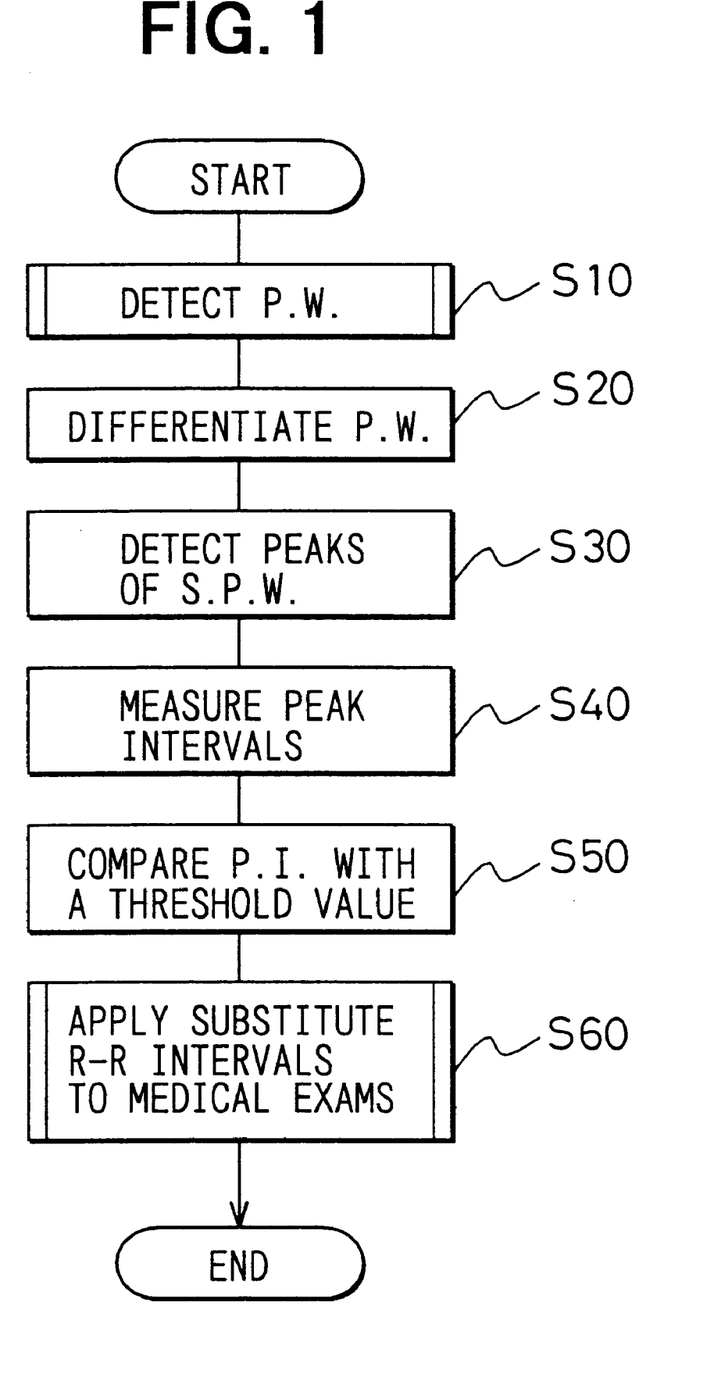
FIG. 1 is a flow diagram showing steps of executing a method of obtaining information that corresponds to the R—R interval of electrocardiogram from a pulse-wave of a human body according to a first embodiment of the invention.
Figure 3A:
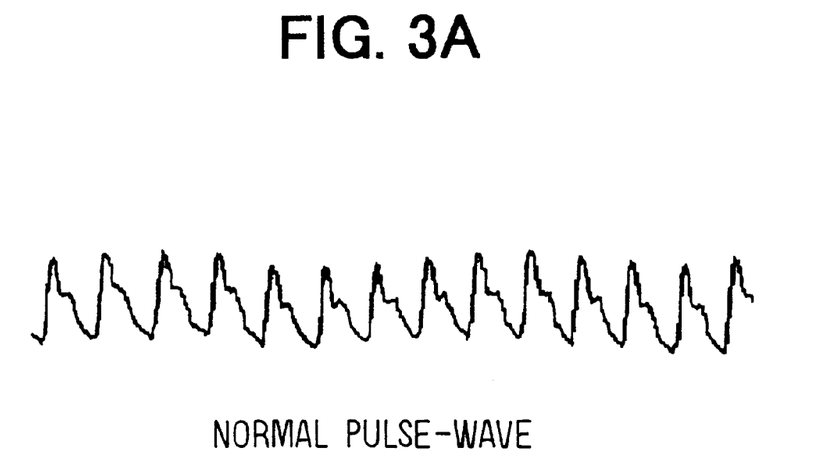
FIGS. 3A and 3B are graphs respectively showing a pulse-wave and a speed-pulse-wave.
Figure 3B:
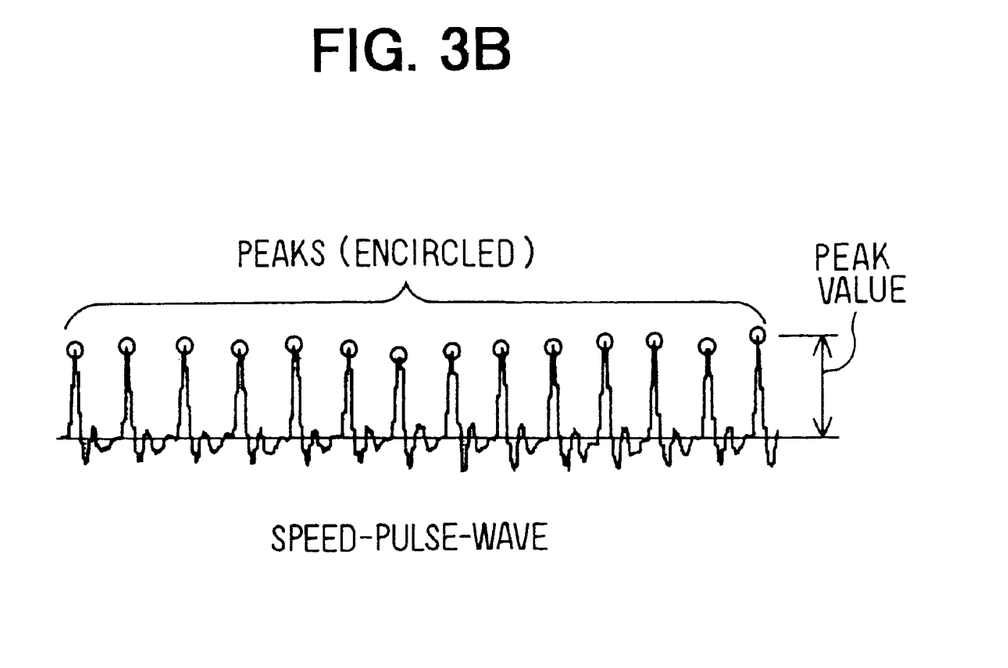

As shown in FIG. 1, the pulse-wave is detected during a predetermined period (e.g. 10 seconds) at S10. The detected pulse-wave is differentiated to provide a speed-pulse-wave at S20, which is shown in FIG. 3B. At S30, the peak value of each pulsation of the speed-pulse-wave is measured during the predetermined period. At S40, peak intervals between adjacent peaks of the speed-pulse-wave are measured. At S50, the peak intervals of the speed-pulse wave are compared with a threshold value that is calculated from the mean value of the measured peak intervals. If some of the peak intervals are equal to or larger than the threshold value, they are selected to obtain pulse wave R—R intervals. At S60, the pulse wave R—R intervals are applied to the medical or health examination. The program is repeatedly executed to continuously monitor the health condition of a person.

Figure 4:
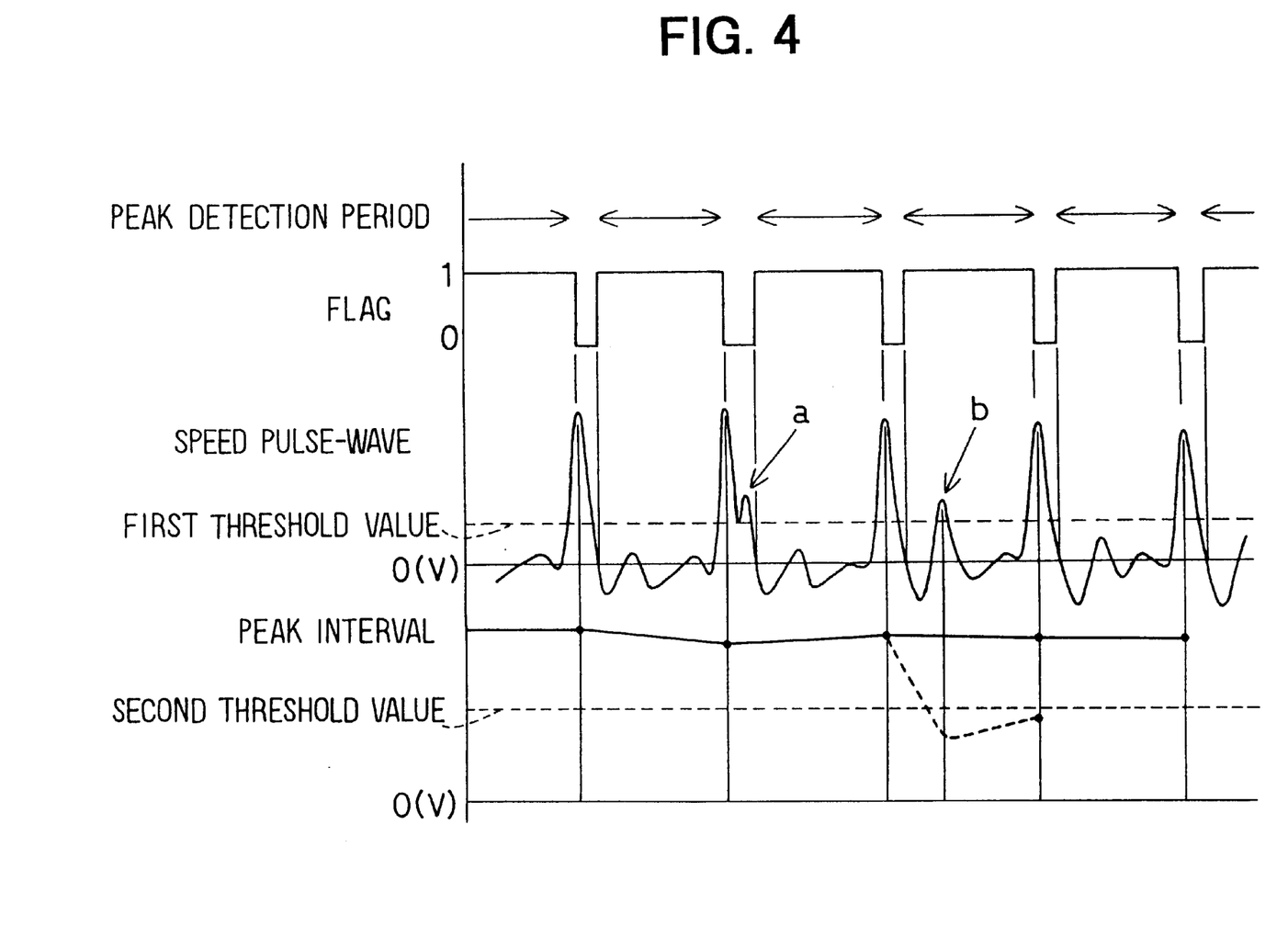
FIG. 4 is a time chart illustrating peak detection ranges of the speed-pulse-wave.

As shown in FIG. 4, the peak values are detected by using a peak flag. The peak flag changes from "0" to "1" when the speed-pulse-wave becomes 0 volt or lower than 0 volt. Thereafter, the flag changes again from "1" to "0" when a peak value of the speed-pulse-wave is detected. That is, the peak values are detected while the peak flag is. "1" (peak detection period). Each peak value is determined if it is larger than some (five, for example) of neighboring values and a first threshold value. This way can exclude error peak values such as point a that appears while the peak detection flag is "0".

The first threshold value is the product of the maximum value of the speed-pulse-waves detected during the predetermined period and a coefficient Ph. The pulse wave R-R intervals are selected at S50 from the peak intervals measured at S40 if the peak intervals are equal to or larger than a second threshold value. Because the peak interval that is calculated from error peak b, as shown in FIG. 4, is smaller than the second threshold value, it is not detected as a real peak value even if it appears. The second threshold value is the product of the mean value of the peak intervals detected during a predetermined period and a coefficient Pt.

Figure 5B:
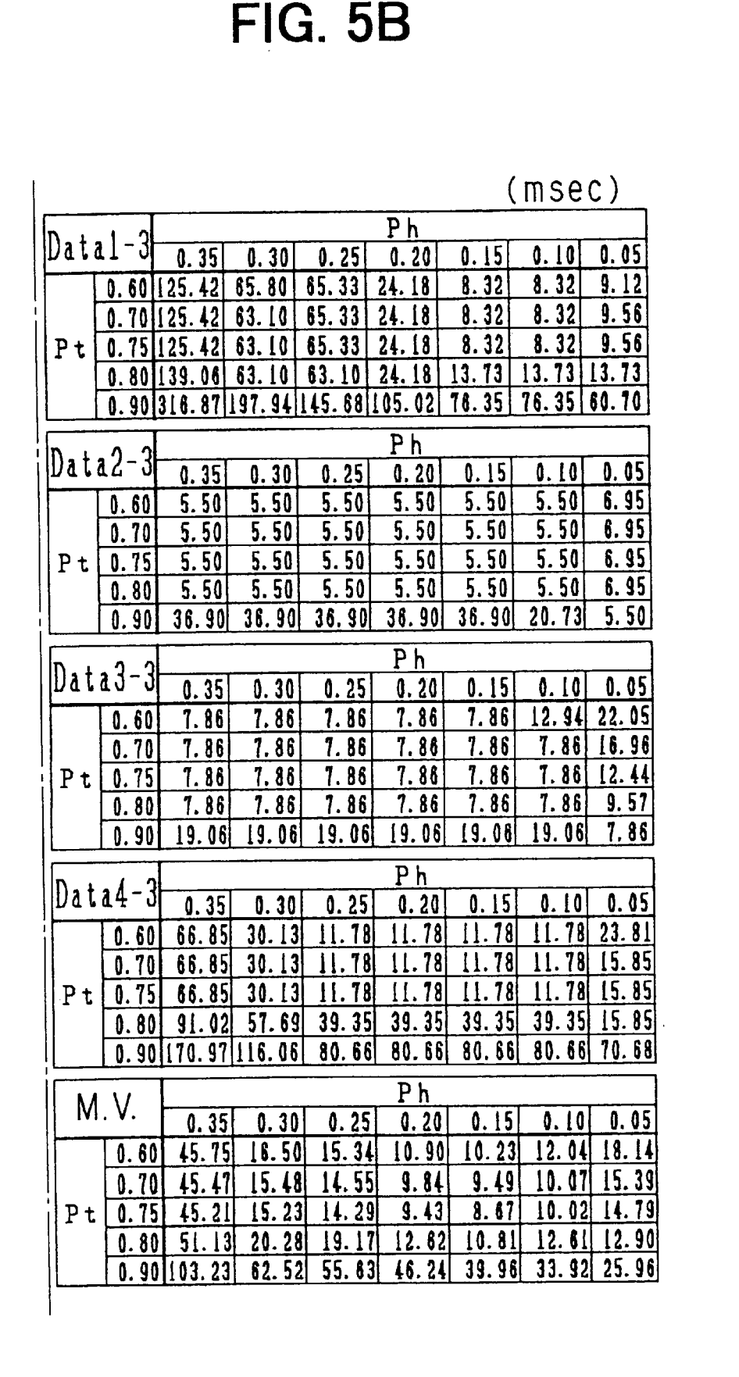
Figure 6:
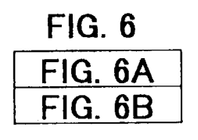
FIGS. 6A and 6B are a table showing test results.
Figure 6A:
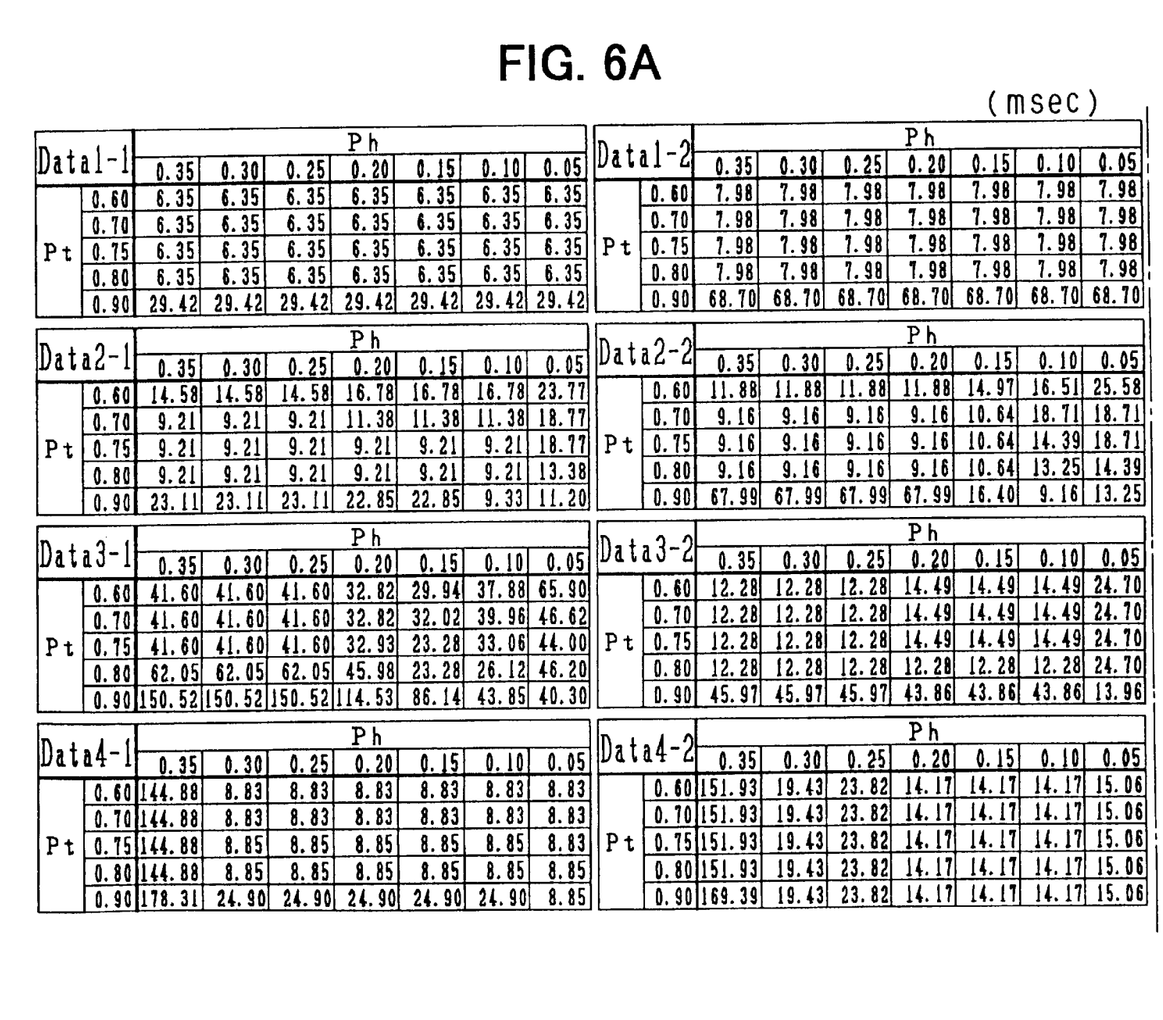
Figure 6B:
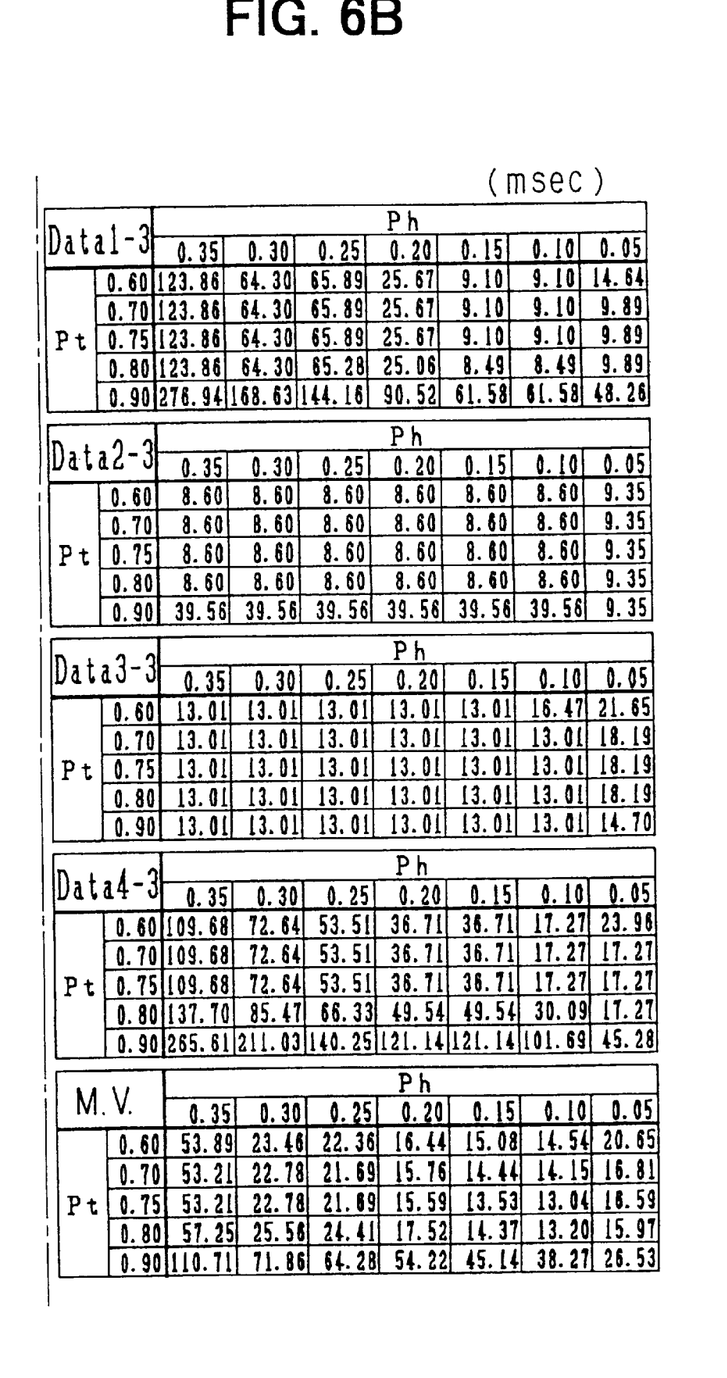
Figure 7B:
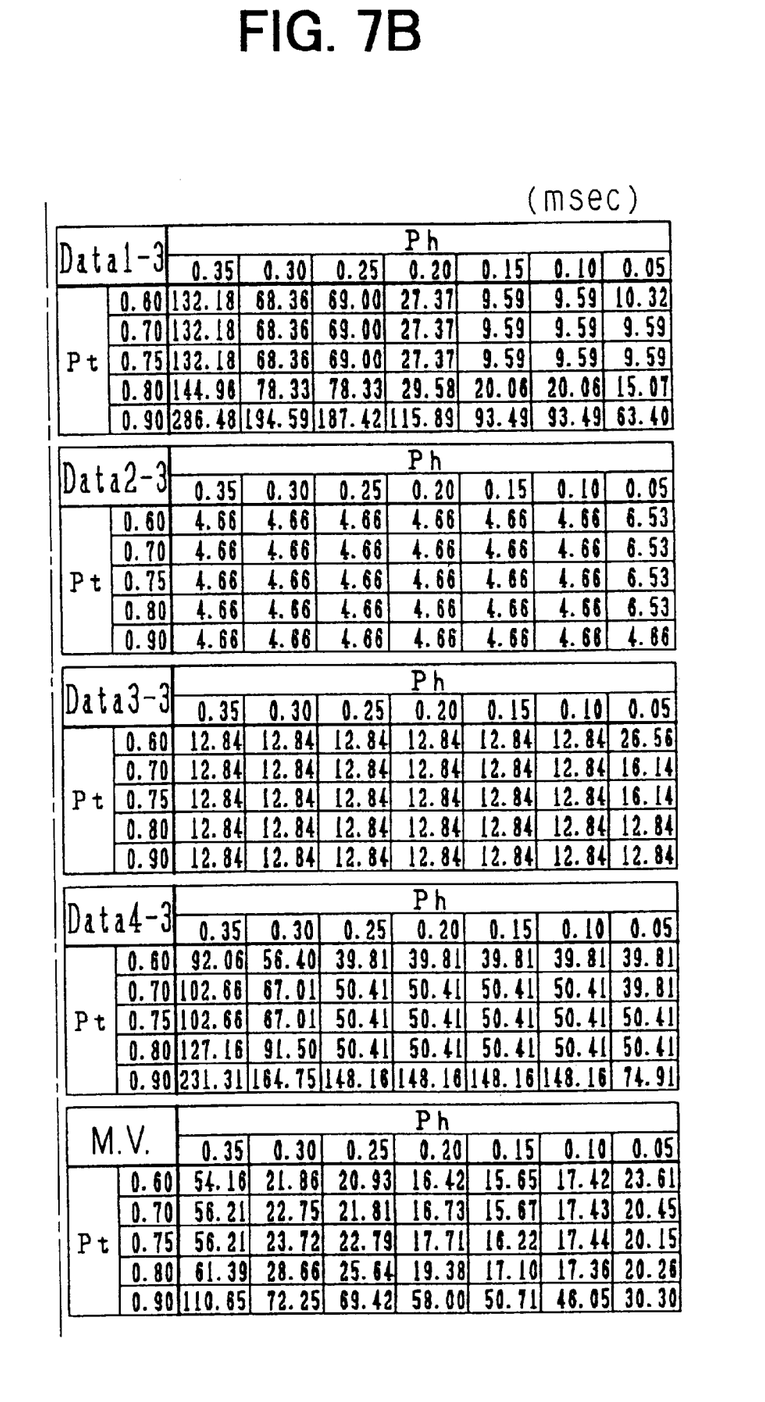

FIGS. 5A and 5B are a table obtained by the method according to the first embodiment of the invention. The table shows differences between the pulse wave R—R interval resampled at intervals of 0.5 sec and the electrocardiogram's R—R interval resampled at intervals of 0.5 sec. It has been noted in the table that the mean value of the differences is the least when the coefficient Ph is 0.15, and the coefficient Pt is 0.75. That is, if the coefficient Ph is 0.15, and the coefficient Pt is 0.75, the pulse wave R-R interval can be most appropriately substituted for the electrocardiogram's R-R interval.

The method according to the first embodiment of the invention is compared with other two methods, which are as follows:

(1) pulse wave R-R intervals are represented by the interval between the negative-to-positive cross points of the speed-pulse-wave; or (2) pulse wave R-R intervals are represented by the interval between the positive-to-negative cross points of the speed-pulse-wave.

FIGS. 6A–6B and 7A–7B are tables respectively obtained by the methods (1) and (2). The tables respectively show differences between the pulse wave R-R intervals resampled at intervals of 0.5 second and the electrocardiogram's R-R intervals resampled at intervals of 0.5 second.

It is noted that the pulse wave R-R interval obtained by the method according to the first embodiment is closer to the electrocardiogram's R-R interval than the pulse wave R-R intervals obtained in the methods (1) and (2).

Figure 8:
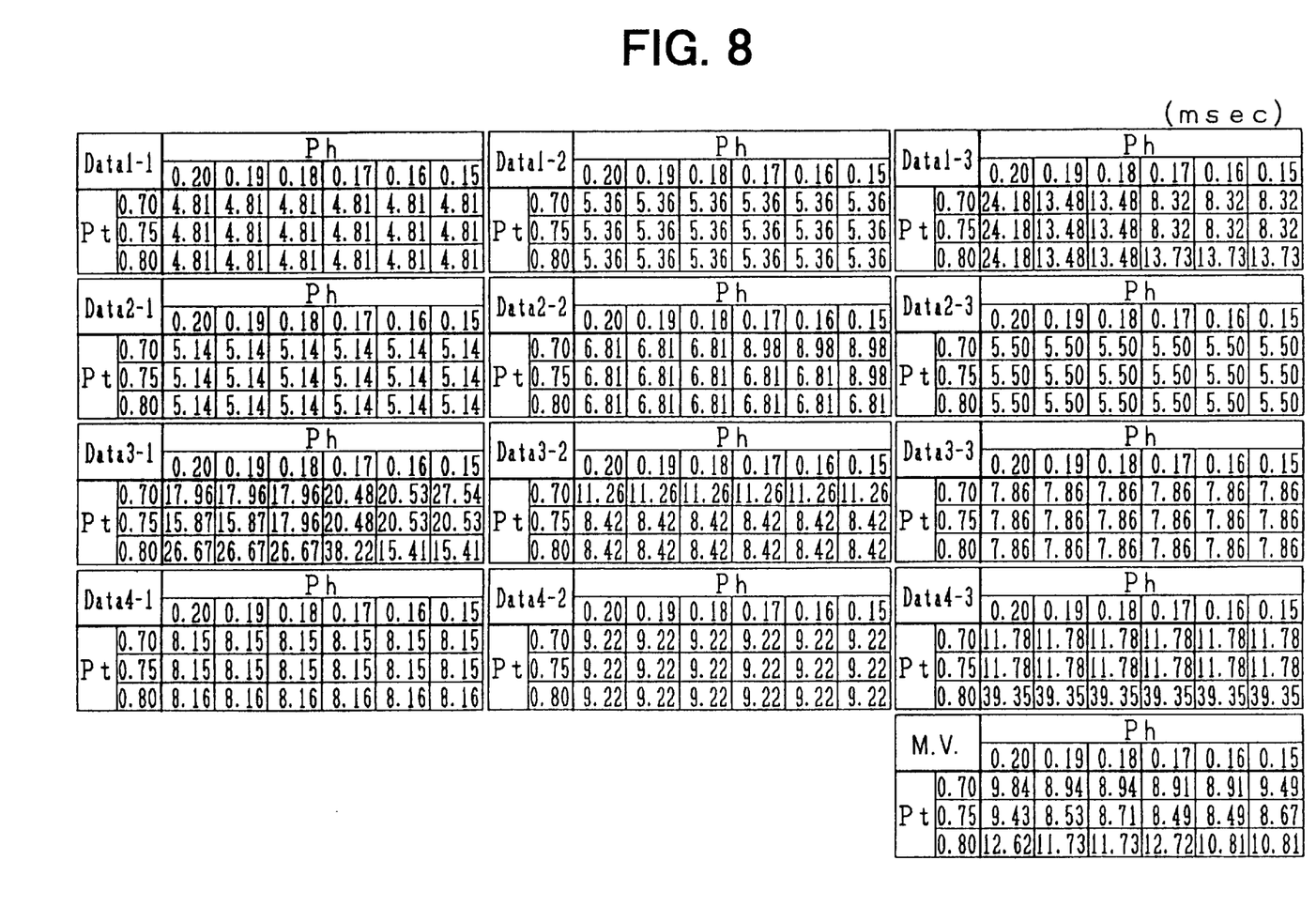
FIG. 8 is a table showing test results

After further investigation, as shown in FIG. 8, it has been found that the pulse wave R-R intervals can be made closer to the electrocardiogram's R-R interval if the coefficient Ph is set to 0.16 or 0.17 (i.e. between 0.16 and 0.17) and Pt is set to 0.75.

Figure 9:
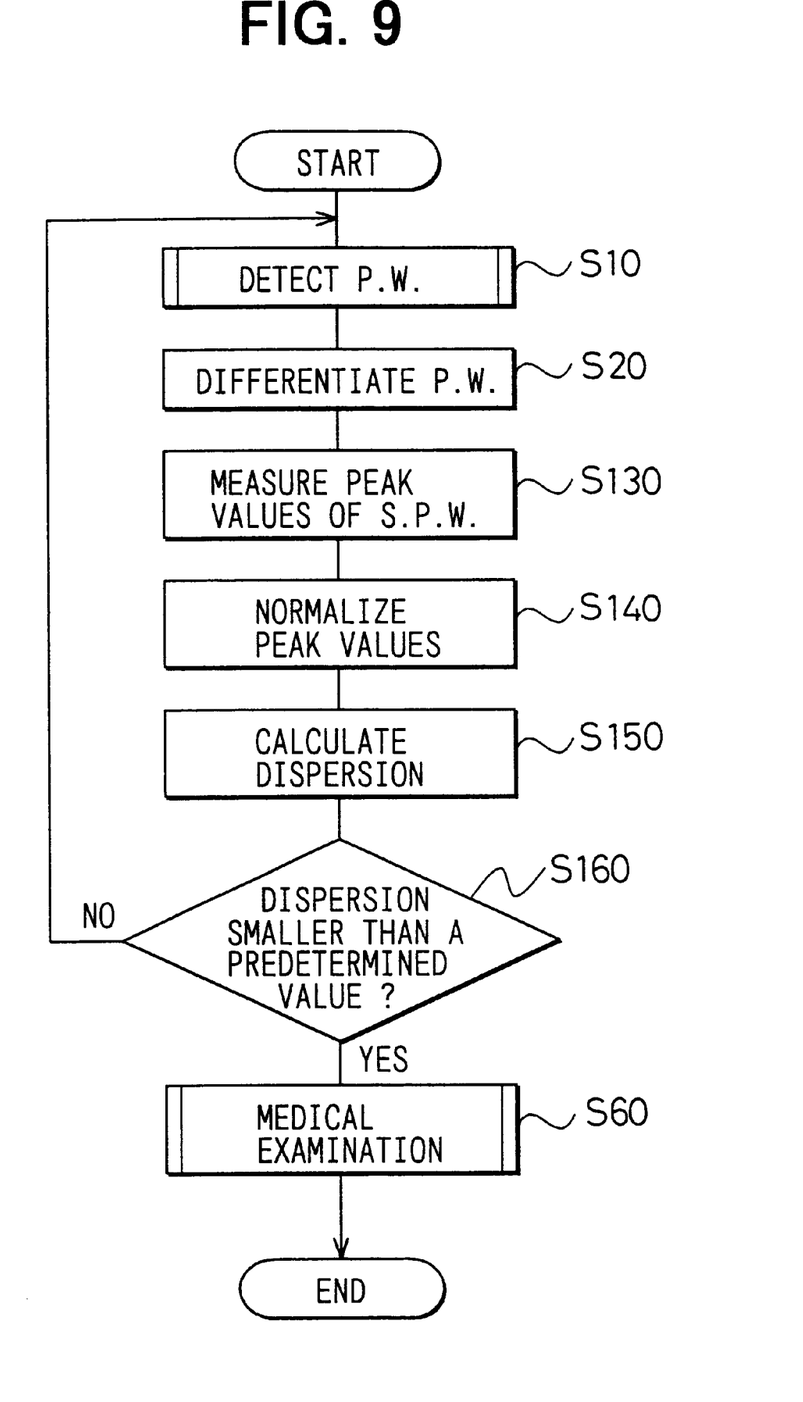
FIG. 9 is a flow diagram showing steps of executing a method of obtaining information that corresponds to the R-R interval of electrocardiogram from a pulse-wave of a human body according to a second embodiment of the invention.

A diagnosis system according to a second embodiment of the invention is substantially the same in construction as the first embodiment shown in FIG. 2 except that the microcomputer provided with a noise detecting program, which is shown in FIG. 9.

Figure 10A:
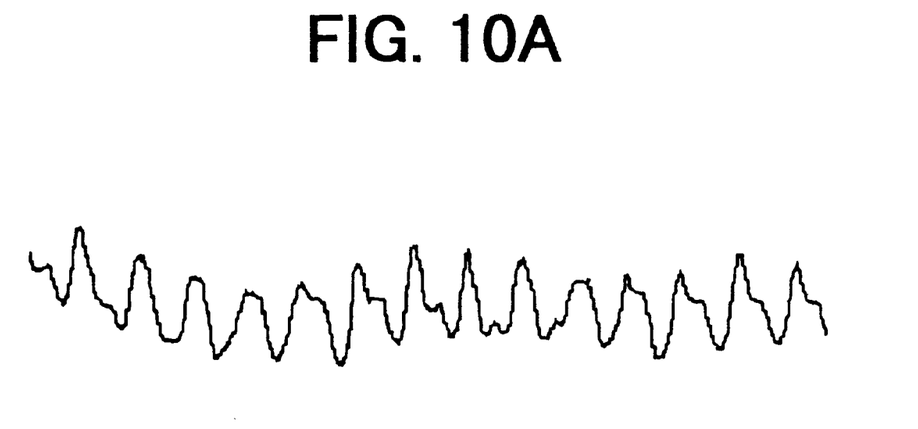
FIGS. 10A and 10B are graphs respectively showing a pulse-wave that includes noises and the speed-pulse-wave thereof.
Figure 10B:
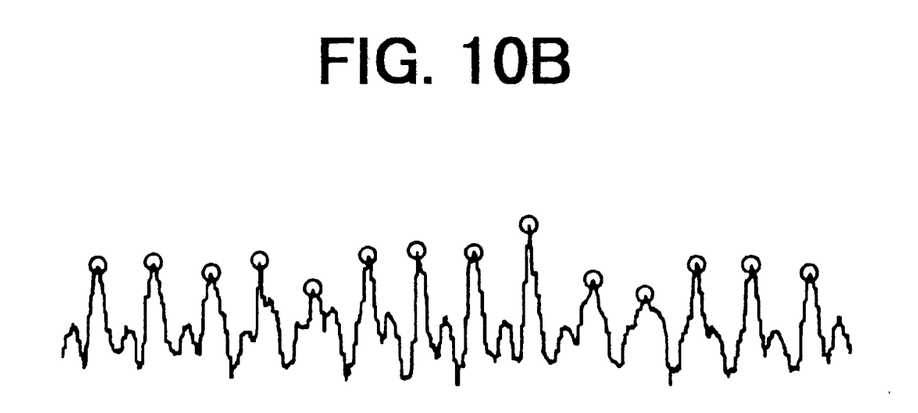

At S10 in FIG. 9, the pulse-wave is sensed by pulse-wave sensor 2 for a predetermined period, e.g. 10 seconds. Thereafter at S20, the detected pulse-wave is differentiated to provide the speed-pulse-wave. At S130, the peak values for the predetermined period are measured. Because the measurement unit and the absolute values of the peak values change with measuring systems, the measured peak values are normalized by the mean value thereof at S140. At S150, the peak values are statistically processed to convert the dispersion thereof to a numerical value. For example, the dispersion is converted into a numerical variance or standard deviation. Subsequently, the numerical value is compared with a preset value at S160. If the numerical value is calculated as standard deviation smaller than the preset value, such as a value equal to 0.1 or 0.5 or between 0.1 and 0.15 in the standard deviation (YES), it is determined that any noise is not practically included in the pulse-wave. Such normal pulse-wave is shown in FIG. 3A, and its speed-pulse-wave is shown in FIG. 3B. In the case of FIG. 3B, the standard deviation is 0.057. At S60, the data are made available to medical and/or health examination. Thereafter the program ends. On the other hand, if the numerical value is not smaller than the preset value (NO) at S160, it is determined that some noises are included in the pulse-wave. Such noise-affected pulse wave is shown in FIG. 10A and its speed-pulse-wave is shown in FIG. 10B. In the case of FIG. 10B, the standard deviation is 0.321. Subsequently, the program turns back to S10.

Figure 11:
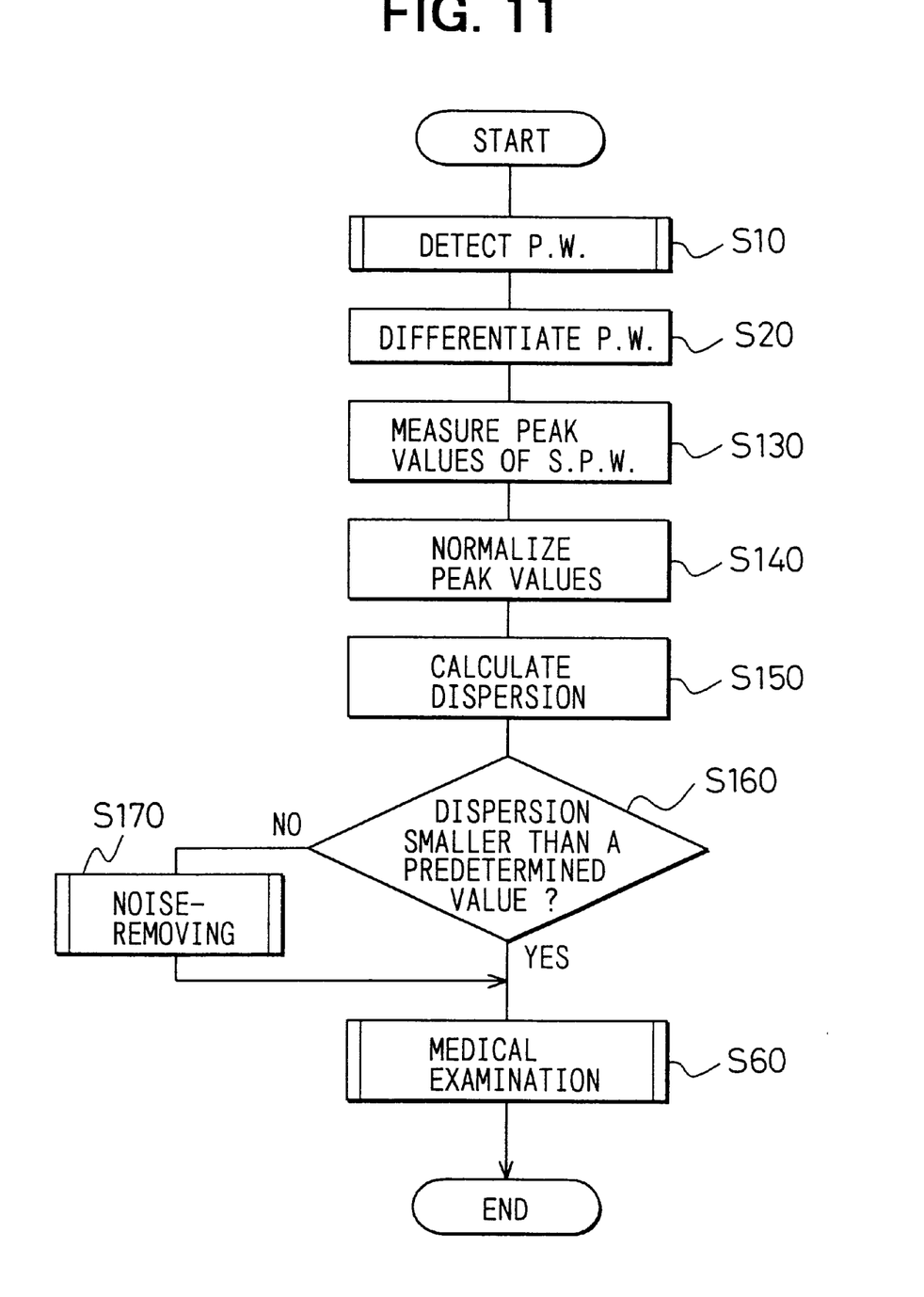
FIG. 11 is a flow diagram showing a variation of the method according to the second embodiment of the invention.

However it is possible to use a digital filter to remove such noises at S170, as shown in FIG. 11.

If the diagnosis system is fixed, it is not necessary to normalize the peak values of S140.

The dispersion of the peak values can be determined by using a variance. In the case of FIG. 3B, the variance of the peak values is 0.003. On the other hand, the variance of the peak values is 0.103 in FIG. 10B.

In this way, if the pulse-wave includes noises, the dispersion becomes large.

It is possible to determine the dispersion of the peak values from the difference between the maximum value and the minimum value of the peak values of the pulse wave.

Light-reflection type pulse-wave sensor 2 can be substituted by a light-transmission type sensor. The pulse-wave sensor can be attached to an ear lobe.

In the foregoing description of the present invention, the invention has been disclosed with reference to specific embodiments thereof. It will, however, be evident that various modifications and changes may be made to the specific embodiments of the present invention without departing from the broader spirit and scope of the invention as set forth in the appended claims. Accordingly, the description of the present invention is to be regarded in an illustrative, rather than restrictive, sense.

What is claimed is:

1. A method of obtaining information that corresponds to an R-R interval of electrocardiogram from a pulse-wave of a human body, said method comprising the steps of:

detecting said pulse-wave of the human body in a predetermined period;

differentiating said detected pulse-wave to provide a speed-pulse-wave;

taking points of said speed-pulse-wave into peak values on the basis of a first threshold value;

measuring intervals of said peak values; and substituting said intervals for the R-R interval of said electrocardiogram.

2. The method as claimed in claim 1, wherein said intervals of said peak values is substituted only when said intervals of said peak values are equal to or larger than a second threshold value.

3. The method as claimed in claim 2, wherein said first threshold value is calculated from said speed-pulse-wave.

4. The method as claimed in claim 2, wherein said first threshold value is calculated from a maximum value of said intervals of peaks of said speed-pulse-wave.

5. The method as claimed in claim 2, wherein said first threshold value is a product of a maximum value of said speed-pulse-wave and a value equal to or larger than 0.16 or equal to or smaller than 0.17.

6. The method as claimed in claim 2, wherein said first threshold value is calculated from said intervals of said peak values of said speed-pulse-wave.

7. The method as claimed in claim 2, wherein said second threshold value is calculated from a mean value of said intervals of said peak values of said speed-pulse-wave.

8. The method as claimed in claim 2, wherein said first threshold value is a product of a mean value of said intervals of said peak values and 0.75.

9. The method as claimed in claim 2, wherein said first threshold value is calculated from said speed-pulse-wave, and said second threshold value is calculated from a peak interval of said pulse-speed-wave.

10. The method as claimed in claim 2, wherein said first threshold value is calculated from a maximum value of said intervals of said peak values of said speed-pulse-wave, and said second threshold value is calculated from said intervals of said peak values of said pulse-speed-wave.

11. The method as claimed in claim 2, wherein said first threshold value is a product of a maximum of said intervals of said peak values of said speed-pulse-wave and a value equal to 0.16, 0.17 or between 0.16 and 0.17, and said second threshold value is determined according to said intervals of said peak values.

12. The method as claimed in claim 2, wherein said first threshold value is calculated from said speed-pulse-wave, and said second threshold value is calculated from a mean value of said intervals of said peak values of said speed-pulse-wave.

13. The method as claimed in claim 2, wherein said first threshold value is calculated from a maximum of said peak values of said speed-pulse-wave, and said second threshold value is calculated from a mean value of said intervals of said peak values of said speed-pulse-wave.

14. The method as claimed in claim 2, wherein said first threshold value is a product of a maximum of said intervals of said peak values of said speed-pulse-wave and a value equal to 0.16, 0,17 or between 0.16 and 0.17, and said second threshold value is calculated from a mean value of said intervals of said peak values of said speed-pulse-wave.

15. The method as claimed in claim 2, wherein said first threshold value is calculated from said speed-pulse-wave, and said first threshold value is a product of a mean value of said intervals of said peak values and 0.75.

16. The method as claimed in claim 2, wherein said first threshold value is calculated from a maximum of said peak values of said speed-pulse-wave, and said second threshold value is a product of a mean value of said intervals of said peak values and 0.75.

17. The method as claimed in claim 2, wherein said first threshold value is a product of a maximum of said peaks of said speed-pulse-wave and a value equal to 0.16, 0.17 or between 0.16 and 0.17, and said second threshold value is a product of a mean value of said intervals of said peak values and 0.75.

* * * * *

UNITED STATES PATENT AND TRADEMARK OFFICE
CERTIFICATE OF CORRECTION

PATENT NO. : 6,496,723 B1
DATED : December 17, 2002
INVENTOR(S) : Taiji Kawachi, Tsuyoshi Nakagawa and Teiyuu Kimura It is certified that error appears in the above-identified patent and that said Letters Patent is hereby corrected as shown below:

<u>Title page,</u>
Item [75], Inventors, delete "Rie Ohsaki, Anjo (JP)"

Signed and Sealed this

Nineteenth Day of August, 2003

JAMES E. ROGAN
*Director of the United States Patent and Trademark Office*